United States Patent [19]

Edman et al.

[11] Patent Number: 4,600,028
[45] Date of Patent: Jul. 15, 1986

[54] SATURATED END WRAP CONSTRUCTION AND COMPOSITION

[75] Inventors: Walter W. Edman; Ernest J. Klemm, both of Westport, Conn.

[73] Assignee: Zotos International Inc., Stamford, Conn.

[21] Appl. No.: 527,039

[22] Filed: Aug. 29, 1983

[51] Int. Cl.$^4$ .......... A45D 7/00; A45D 19/00
[52] U.S. Cl. .......... 132/7; 424/70; 424/72
[58] Field of Search .......... 132/7; 424/70, 72, 71

[56] References Cited

U.S. PATENT DOCUMENTS

| | | | |
|---|---|---|---|
| 2,564,722 | 8/1957 | Reed et al. | 132/7 |
| 2,631,965 | 3/1953 | Schnell | 424/72 |
| 2,688,972 | 9/1954 | Brown | 132/7 |
| 2,719,814 | 10/1955 | Haefele | 424/71 |
| 2,832,357 | 4/1958 | Powers | 424/70 |
| 2,839,066 | 6/1958 | Sanders | 424/72 |
| 2,869,559 | 1/1959 | Moore | 132/7 |
| 2,991,790 | 7/1961 | Bonilla | 132/9 |
| 3,087,501 | 4/1963 | Rosmarin | 424/70 |
| 3,087,502 | 4/1963 | Rosmarin | 424/71 |
| 3,087,503 | 4/1963 | Rosmarin | 424/71 |
| 3,345,993 | 10/1967 | Haefele | 132/7 |
| 3,367,345 | 2/1968 | Riley | 132/9 |
| 3,465,759 | 9/1969 | Haefele | 132/7 |
| 3,548,842 | 12/1970 | McCall | 132/9 |
| 3,693,633 | 9/1972 | Kalopissis et al. | 132/7 |
| 3,768,490 | 10/1973 | Kalopissis et al. | 132/7 |
| 3,955,586 | 5/1976 | Hartsough | 132/7 |
| 3,957,065 | 5/1976 | Busch et al. | 424/70 |
| 4,044,782 | 8/1977 | Adrion et al. | 132/7 |
| 4,105,038 | 8/1978 | Adrion et al. | 132/7 |
| 4,130,121 | 12/1978 | Wetzel | 132/7 |
| 4,158,704 | 6/1979 | Baer et al. | 424/72 |

FOREIGN PATENT DOCUMENTS 1531965  1/1941  United Kingdom .......... 132/9

*Primary Examiner*—Andrew H. Metz
*Assistant Examiner*—Helane Myers
*Attorney, Agent, or Firm*—Mattern, Ware, Stoltz & Fressola

[57] ABSTRACT

By providing high absorbent end wraps staturated with a disulfide, the action of the reducing agent on the porous ends of the hair is controlled, typical overprocessing of the hair ends is eliminated, and a uniform permanently waved head of hair is obtained. Preferably the disulfide saturated into the end wraps is the disulfide of the mercaptan used in the permanent waving lotion.

9 Claims, No Drawings

SATURATED END WRAP CONSTRUCTION AND COMPOSITION

TECHNICAL FIELD

This invention relates to the art of permanent waving of hair, and more particularly to unique saturated end wrap constructions, compositions, methods of manufacture and use.

BACKGROUND ART

As is well known, hair is composed of a unique protein material, called "keratin", which is distinguished by the fact that it contains a very significant amount of an amino acid (cystine) which contains the element sulfur in addition to the elements nitrogen, oxygen, carbon and hydrogen. In the structure of hair, the cystine covalently links adjacent polypeptide chains (K) through two sulfur atoms (S-S). These disulfide bonds can be broken only by specific chemical action.

Similarly, it is well established that in order to permanently wave hair this disulfide linkage must be broken. In this regard, many prior art compositions have been developed for the "cold permanent waving" of hair. Typically, these prior art systems treat the hair with a reducing agent which breaks the disulfide (cystine) linkages in the hair while the hair is wound around a curling rod. These prior art systems are typified by the disclosures in U.S. Pat. Nos. 2,479,382, 2,688,972, and 2,708,940.

As discussed in these prior art patents, the reducing agent typically employed is a mercaptan. The chemistry involved in the reaction of a mercaptan with the cystine disulfide bonds in the hair fiber is illustrated by the following chemical equation:

$$KSSK + 2\ RSH \rightleftharpoons 2\ KSH + RSSR$$

By rebonding the sites in the reduced keratin in their new curled configuration, a permanent set which is impervious to water is established.

The rebonding of the reduced sites is accomplished by the action of a chemical oxidizing agent, commonly referred to as the permanent wave neutralizer. Typically, the oxidizing agent used in most neutralizers is hydrogen peroxide, and its chemical reaction is illustrated in the following equation:

$$2\ KSH + H_2O_2 \rightarrow KSSK + 2\ H_2O$$

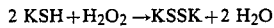

A problem encountered with the use of mercaptan reducing agents for the permanent waving of hair is that one lotion strength is needed for normal hair while a different lotion strength is needed for damaged or difficult to wave hair. This problem is further compounded when there is damaged as well as normal hair on a head of hair to be permanently waved.

In general, damaged hair fibers and relatively undamaged hair fibers coexist on almost every head. Since the hair grows outwardly from the scalp, it is constantly being subjected to mechanical damage, particularly from the normal grooming process of shampooing, combing, drying, and brushing. In addition to this physical damage of hair, hair is also damaged by chemical action such as by exposure to sunlight and contact with water containing chlorine.

Damage to the hair fiber is almost entirely directed against the hair cuticle. In shampooing, for example, it is the actual physical manipulation of the hair, rather than the shampoo itself, which causes the majority of the damage. In normal hair, which has six to seven cuticle layers at the new growth or scalp area, studies have shown that a normal shampoo process can break away the cuticle at the rate of 1 to 2.5 cuticles for every fifty treatments. Since it is not unusual for a woman to shampoo her hair every day, it is therefore possible that she could lose up to seven cuticle layers of her hair in five months.

Since hair normally grows approximately one-half inch each month, it is apparent that in five months, all of the hair longer than two and one-half inches would be denuded of the cuticle layer. In addition, since the cuticle comprises ten percent or more of the hair fiber, and a much higher percentage in fine hair, and is intended to act as a protective sheath about the cortex, its complete destruction represents formidable damage to the hair fiber. Once the hair fiber has lost part or all of its cuticle, it is classified as porous and readily absorbs any aqueous solution applied to it.

During most permanent wave applications, a tress of the hair is wrapped around a cylindrical rod or curler. However, difficulty is often encountered in wrapping the free ends of the hair tress on the curler. Consequently, small square or rectangular pieces of paper, commonly referred to in the trade as "end wraps" are folded over the ends of the hair tress in order to make the hair controllable and easily rolled about a curler. Although end wraps are typically formed from paper or fabric material, various other compositions such as polyurethane foam and impermeable plastic foam are disclosed in such patents as U.S. Pat. Nos. 3,345,993 and 3,465,759.

Typical prior art cold permanent waving solutions have been unable to satisfy the diverse conditions which exist along the length of hair fiber to produce a uniform permanently waved head of hair. Typically, depending upon the concentration of the lotion applied to the head of hair, particular segments of the hair are either under processed or over processed.

Many prior art attempts have been made to eliminate the inherent difficulty encountered from the overprocessing and underprocessing of various segments of the hair during a permanent wave application. These prior art attempts included the application of various compositions to the end wrap in order to separately treat the portions of the hair fibers coming in contact with the end wraps. These prior art attempts included applying oils, perfumes, lanolin, diluted waving lotions, and vitamin compositions to the end wrap, all in an attempt to prevent the undesirable overprocessing of the hair ends. These prior art products are disclosed in U.S. Pat. Nos. 2,832,357; 2,839,066; 2,991,790; 3,087,501; 3,087,502; and 3,087,503.

In spite of the extensive effort directed to the protection of the hair ends in cold permanent waving procedures, none of these prior art systems have achieved the desired results. Consequently, continued over-exposure of the hair ends is typically encountered with the adverse appearance resulting therefrom.

Consequently, it is a principal object of the present invention to provide unique, saturated end wraps which prevent the overprocessing of hair ends during the application of a cold permanent wave.

Another object of the present invention is to provide unique, saturated end wraps having the characteristic features described above which produce a substantially uniform permanent wave throughout the head of hair regardless of the damaged condition of portions of the hair fiber.

Another object of the present invention is to provide unique saturated end wraps having the characteristic features described above which are easily employed, without special training, and with any cold permanent hair waving system.

Other and more specific objects will in part be obvious and will in part appear hereinafter.

DISCLOSURE OF INVENTION

By employing the unique, saturated end wraps of this invention, the continuing difficulties found in the prior art are eliminated. Now, for the first time, the commonly experienced problems of underprocessing and overprocessing hair fibers during the application of a cold permanent wave are eliminated, and a uniform permanent wave is achieved.

In the present invention, end wraps are saturated with a chemical which controls the action of the reducing agent on the porous ends of the hair fiber. This chemical takes advantage of the fact that the chemical equation for the cold wave reducing action is a reversible reaction, which at equilibrium is proceeding at equal speed in both directions.

Using the present invention, the end wraps are saturated with a disulfide (RSSR). By then applying these saturated end wraps to the hair, the equilibrium of the chemical equation defining the cold wave reducing action is shifted to the left at the ends of the hair. In this way, the number of disulfide bonds (cystine) that are broken on the ends of the hair are reduced.

The efficacy of the present invention is clearly borne out by the Mass Action Law which states that the equilibrium point of a chemical reaction is altered by changing the concentration of the reactants on either side of the chemical equation. Consequently, by saturating end wraps with a disulfide and applying the end wraps to the ends of the hair in the conventional manner, the chemical reaction occurring at the hair ends possess an increased concentration of the disulfide (RSSR) on the right side of the chemical equation. As a result, the equilibrium of the reaction at the hair ends is forced to the left, thus reducing the number of disulfide bonds (cystine) that will be broken. In addition, since the mercaptan reducing agent forming a part of the cold wave lotion is applied throughout the head of hair in the conventional manner, the remainder of the hair is processed normally, receiving its normal permanent wave, with only the hair ends being protected from overprocessing.

Typically, human hair contains about seventeen percent to eighteen percent cystine and it has been found that to get an optimum permanent wave, sufficient bonds must be broken. If excess bonds are broken, the hair will be overprocessed and damaged. If insufficient bonds are broken, the hair will be underprocessed and the wave will relax in a short time.

Normally, an operator determines when the optimum wave is reached by partly unrolling one curl during the processing time and, from past experience, makes a judgment when an optimum wave has been attained. However, it is impossible for the operator to judge how the ends of the hair have processed, since the hair ends are not exposed in the curl evaluation.

Furthermore, prior to the present invention, there was no end wrap an operator could use to equalize the waving lotion action so that it processes the ends of the hair to the same degree as the new growth. As a result, prior art permanent wave systems are typically overprocessed at the ends of the hair, and show all the attributes of overprocessed damaged hair, namely, frizziness, dryness and split ends. However, by employing the teaching of the present invention and applying end wraps which have been saturated with a disulfide, equal processing of the entire head of hair is achieved and overprocessing is eliminated.

Although any water-soluble disulfide can be employed in the present invention, the preferred composition comprises the disulfide of the mercaptan used in the waving solution. In this way, greatest efficacy is achieved.

Typical mercaptans used in waving solutions are the salts or esters of thioglycolic acid. Thus, in the preferred embodiment, the oxidation product of these mercaptans are saturated in the end wraps of this invention. These typical disulfides are diammonium dithiodiglycolate or diglyceryl dithiodiglycolate. Since these salts and esters are very soluble, they are immediately absorbed into the porous ends of the hair fiber, where they control the reducing action of the respective mercaptan reducing agents used in the cold wave lotion, thereby providing the desired reduction in the breakage of the disulfide bonds.

The end wraps may comprise either paper or fabric. However, it is preferred that a highly absorbent paper be employed which also has a high wet strength. In addition, the end wrap must be of a size and shape that will at least partially encircle the tress of hair. Preferably, the end wrap has either a square or rectangular shape and has dimensions ranging between about one and one-half inches by one and one-half inches to about four inches by four inches. An especially preferred size and configuration is a rectangular shaped paper having a dimension of three and one-half inches by two inches. The preferred thickness of the paper ranges between 0.0010 to about 0.0030 inches.

The invention accordingly comprises the several steps and the relation of one or more of such steps with respect to each of the others, and the article possessing the features, properties, and the relation of elements, which are exemplified in the following detailed disclosure, and the scope of the invention will be indicated in the claims.

BEST MODE FOR CARRYING OUT THE INVENTION

Construction of the saturated end wraps of the present invention can be carried out in a variety of alternate ways. Principally, end wraps as taught herein may be manufactured and distributed as part of the permanent waving system, or the user of a permanent wave system may be instructed in the method for making the end wraps of the present invention as part of the permanent wave application. Preferably, the saturated end wraps of this invention are constructed and distributed with the permanent waving system in order to assure quality control and product uniformity, as well as provide easy adoption and use of the saturated end wraps of the present invention as part of the permanent waving application.

The preferred method for making the saturated end wraps of the present invention is to submerge untreated paper or fabric end wraps of the desired size, shape and thickness into a solution containing the desired disulfide. Since the end wraps are highly absorbent, submersion for about one to fifteen seconds has been found to be sufficient for the desired saturation level. Then, the saturated end wrap is removed from the disulfide solution and dried in any one of the conventional ways, such as on a hot roller.

The actual amount of the disulfide absorbed into the end wrap and retained in the dried end wrap has been found to be directly related to the concentration of the disulfide in the solution, as detailed in the following example.

EXAMPLE I

In order to determine the amount of disulfide absorbed by an untreated end wrap, uniform pieces of paper having a size of two inches by three and one-half inches and a uniform thickness of between about 0.0010 and 0.0030 inches, were submerged into different solutions each containing ten percent, twenty percent, thirty percent or forty percent of diammonium dithiodiglycolate and dried on a hot roller. As shown in TABLE I, four different solutions of diammonium dithiodiglycolate were employed. As shown in the results tabulated in TABLE I, the dried end wraps absorbed the disulfide at a rate directly proportional to the concentration of the solution.

TABLE I

| Disulfide Solution | Untreated End Wrap (Wt.) | Treated End Wrap (Wt.) | Wt. of Disulfide |
| --- | --- | --- | --- |
| 10% solution | 0.05 gm | 0.07 gm | 0.02 gm |
| 20% solution | 0.05 gm | 0.09 gm | 0.04 gm |
| 30% solution | 0.05 gm | 0.11 gm | 0.06 gm |
| 40% solution | 0.05 gm | 0.13 gm | 0.08 gm |

In order to determine the optimum amount of disulfide which should be contained in the end wrap of the present invention to obtain the desired results, it must be remembered that in a permanent wave procedure, the hair is divided into fifty to one-hundred sections, depending on the style desired. As a result, between about fifty and one-hundred end wraps would be used to wind the head of hair on curling rods. In addition, in a normal head of hair, approximately 100 cc's of waving lotion is required to wave hair.

Employing these general statistics, it is apparent that each wound tress will receive between about 1 cc and 2 cc's of lotion. Since waving lotions normally comprise approximately eight percent by weight of the active reducing agent, each tress receives between about 0.08 and 0.16 grams of the reducing agent. It has been found that to be effective, each end wrap should contain between about 0.002 grams and 0.08 grams of disulfide.

EXAMPLE II

Hair on a human head was shampoed and towel-dried and then parted and sectioned into seventy strands. Half (35) of the strands were treated with end wraps saturated with the twenty percent solution of the disulfide detailed in TABLE I. The other half of the strands were wrapped with untreated end wraps.

The end wraps were folded transversely across the ends of the strands of hair and then wound on curling rods. After the hair was entirely wound up in this manner and fastened in place, the wound hair was saturated with the reducing lotion detailed in TABLE II. The hair was then allowed to stand for a period of time go get an optimum wave.

On normal hair, the optimum wave generally forms in about ten minutes. When the optimum wave was reached, the entire head was thoroughly water-rinsed and then each curl was treated with the neutralizing lotion, detailed in TABLE III, to oxidize the reduced keratin back to keratin disulfide in the new curl configuration. The curls were then loosened and thoroughly water-rinsed.

TABLE II

| | |
| --- | --- |
| Ammonium Thioglycolate | 8.0% |
| Ammonia | 1.2% |
| Water | 90.8% |

TABLE III

| | |
| --- | --- |
| Hydrogen Peroxide | 2.3% |
| Water | 97.7% |

As the hair is unwound from the curlers, it retains a new curl configuration conforming to the diameter of the curling rod. The ends of the hair showed a marked difference in strands wound with treated end wraps to those wound with the untreated end wraps. The hair wound with the treated end wraps was completely free of frizziness and split ends. The damage to the ends was reduced and the hair in this area was free from snarls, characteristic of broken ends. The hair wound with the untreated end wraps showed all the attributes of damaged hair, namely, frizziness, dryness and split ends.

It will thus be seen that the objects set forth above, among those made apparent from the preceding description, are efficiently attained and, since certain changes may be made in carrying out the above method and in the articles set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention, what we claim is new and desire to secure by Letters Patent is:

1. A method for permanently waving a head of hair comprising the steps of:
   A. sectioning the head of hair into a plurality of separate hair fiber sections to be curled;
   B. applying an end wrap saturated with a disulfide to the ends of the hair fibers of one section;
   C. winding the disulfide saturated end wrap and the hair fibers onto a curling rod;
   D. fastening the curling rod in place once the entire hair section has been rolled thereon;
   E. repeating step B-D until all of the hair fiber sections and the saturated end wraps have been wound on curling rods;
   F. treating the wound hair on each rod with a permanent waving lotion;
   G. rinsing the entire head of hair with water after the permanent waving lotion has had sufficient time to act on the hair fibers;
   H. drying the rinsed hair with a towel;
   I. applying a neutralizing lotion to the permanently waved head of hair;
   J. loosening all of the wound tresses; and K. thoroughly rinsing the entire head of hair with water.

2. The method defined in claim 1, wherein each staturated end wrap is further defined as containing between about 0.002 grams and 0.08 grams of disulfide.

3. A method for permanently waving hair comprising the steps of:
   A. combing the head of hair to form at least one section of hair fibers to be curled;
   B. applying an end wrap saturated with a disulfide to the ends of the hair fibers of said section;
   C. winding the disulfide saturated end wrap and the hair fibers onto a curling rod;
   D. securing the curling rod in place with the hair fibers rolled thereon; and
   E. treating the wound hair on the rod with a permanent waving lotion.

4. A method for permanently waving a head of hair defined in claim 3, comprising the additional steps of:
   F. combing the head of hair into a plurality of hair fiber sections to be curled;
   G. applying an end wrap saturated with a disulfide to the ends of the hair fibers of each of said sections;
   H. winding the disulfide saturated end wrap and hair fibers of each of said sections onto separate curling rods; and
   I. securing each of the curling rods in place once the section of hair has been rolled thereon.

5. A method for permanently waving a head of hair as defined in claim 3, comprising the additional steps of:
   F. rinsing the hair with water after the permanent waving lotion has had sufficient time to act on the hair fibers;
   G. drying the rinsed hair with a towel;
   H. applying a neutralizing lotion to the permanently waved hair fibers;
   I. loosening the wound tress; and
   J. thoroughly rinsing the hair fibers with water.

6. The method defined in claim 3, wherein said permanent waving lotion is further defined as comprising a mercaptan reducing agent and the disulfide impregnated into the end wrap is further defined as comprising the oxidation product of the mercaptan reducing agent.

7. The method defined in claim 3, wherein said disulfide is further defined as comprising one selected from the group consisting of diammonium dithiodiglycolate and diglyceryl dithiodiglycolate.

8. The method defined in claim 3, wherein said end wrap is further defined as comprising highly absorbent paper having a high wet strength and a size and shape ranging between about one and one-half inches by one and one-half inches and about four inches by four inches.

9. The end wrap defined in claim 3, wherein said end wrap is further defined as comprising the disulfide saturated throughout the entire end wrap.

* * * * *